United States Patent [19]
Green et al.

[11] Patent Number: 5,573,169
[45] Date of Patent: * Nov. 12, 1996

[54] APPARATUS FOR APPLYING TWO-PART SURGICAL FASTENERS IN LAPAROSCOPIC OR ENDOSCOPIC PROCEDURES

[75] Inventors: David T. Green, Westport; Henry Bolanos, East Norwalk; Michael S. Kolesa, Norwalk, all of Conn.; Kenneth Toso, Port Chester, N.Y.

[73] Assignee: United States Surgical Corporation, Norwalk, Conn.

[*] Notice: The portion of the term of this patent subsequent to Mar. 8, 2013, has been disclaimed.

[21] Appl. No.: 253,208

[22] Filed: Jun. 2, 1994

Related U.S. Application Data

[63] Continuation of Ser. No. 955,828, Oct. 2, 1992, abandoned.
[51] Int. Cl.⁶ .................................................. A61B 17/068
[52] U.S. Cl. .................................... 227/177.1; 227/181.1; 227/19
[58] Field of Search ................................. 227/19, 176, 178, 227/180, 181, 176.1, 177.1, 178.1, 181.1

[56] References Cited

U.S. PATENT DOCUMENTS

| | | |
|---|---|---|
| 2,028,635 | 1/1936 | Wappler . |
| 3,079,606 | 3/1963 | Bobrov et al. . |
| 3,490,675 | 1/1970 | Green et al. . |
| 3,499,591 | 3/1970 | Green . |
| 4,111,206 | 9/1978 | Vishnevsky et al. . |
| 4,273,129 | 6/1981 | Boebel . |
| 4,354,628 | 10/1982 | Green . |
| 4,402,445 | 9/1983 | Green . |
| 4,429,695 | 2/1984 | Green . |
| 4,493,322 | 1/1985 | Becht . |
| 4,506,670 | 3/1985 | Crossley . |
| 4,506,671 | 3/1985 | Green . |
| 4,513,746 | 4/1985 | Aranyi et al. . |
| 4,520,817 | 6/1985 | Green . |
| 4,527,724 | 7/1985 | Chow et al. . |
| 4,566,620 | 1/1986 | Green et al. . |
| 4,589,416 | 5/1986 | Green . |
| 4,591,085 | 5/1986 | DiGiovanni . |
| 4,606,345 | 8/1986 | Dorband et al. . |
| 4,608,981 | 9/1986 | Rothfuss et al. . |
| 4,633,861 | 1/1987 | Chow et al. . |
| 4,633,874 | 1/1987 | Chow et al. . |
| 4,665,916 | 5/1987 | Green . |
| 4,728,020 | 3/1988 | Green et al. . |
| 4,741,336 | 5/1988 | Failla et al. . |
| 4,784,137 | 11/1988 | Kulik et al. ............................ 227/19 X |
| 4,796,793 | 1/1989 | Smith et al. ............................... 227/19 |
| 4,807,628 | 2/1989 | Peters et al. . |
| 4,819,853 | 4/1989 | Green ....................................... 227/19 |
| 4,863,088 | 9/1989 | Redmond et al. . |
| 4,869,414 | 9/1989 | Green et al. ............................. 227/19 |
| 4,881,544 | 11/1989 | Green et al. . |
| 4,932,960 | 6/1990 | Green et al. . |
| 5,040,715 | 8/1991 | Green et al. . |
| 5,065,929 | 11/1991 | Schulze et al. . |
| 5,071,430 | 12/1991 | de Salis et al. . |
| 5,083,695 | 1/1992 | Foslien et al. . |
| 5,100,418 | 3/1992 | Yoon et al. . |
| 5,156,315 | 10/1992 | Green et al. . |
| 5,156,614 | 10/1992 | Green et al. . |
| 5,170,925 | 12/1992 | Madden et al. ....................... 227/19 X |
| 5,253,793 | 10/1993 | Green et al. . |
| 5,366,134 | 11/1994 | Green et al. .......................... 227/19 X |
| 5,423,471 | 6/1995 | Mastri et al. .......................... 227/19 X |

FOREIGN PATENT DOCUMENTS 2330182  1/1975  Germany .................................. 227/19

*Primary Examiner*—Rinaldi I. Rada

[57] ABSTRACT

Apparatus is disclosed for applying two-part surgical fasteners during endoscopic or laparoscopic procedures. The apparatus includes a handle portion, an elongated endoscopic portion which extends from the handle portion, and structure associated with a distal end portion of the endoscopic portion for applying a two-part surgical fastener. The fastener applying structure includes a camming assembly for driving the fastener portion of the two-part surgical fastener into engagement with the retainer portion of the two-part surgical fastener through a fastener lifting member.

24 Claims, 16 Drawing Sheets

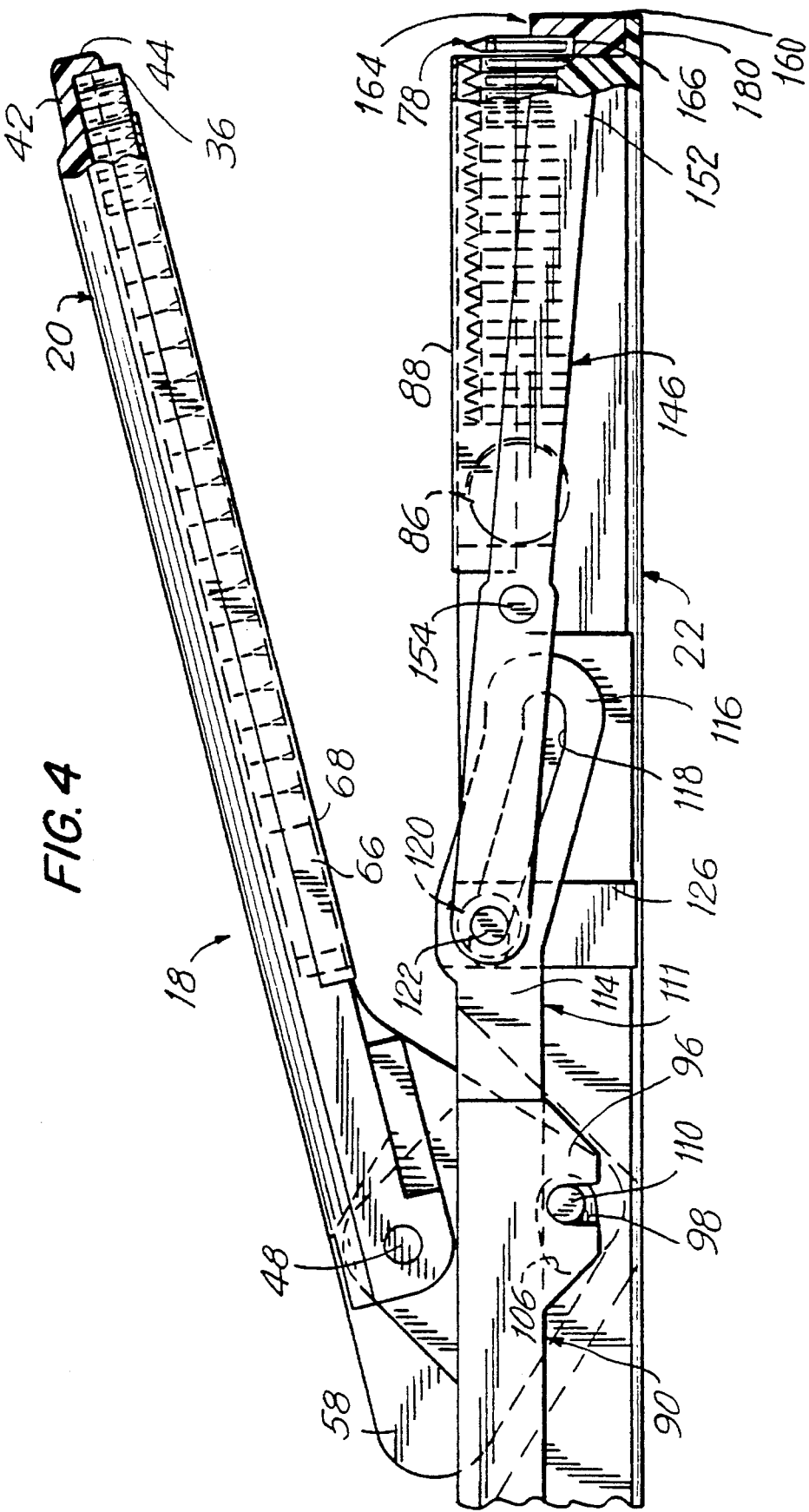

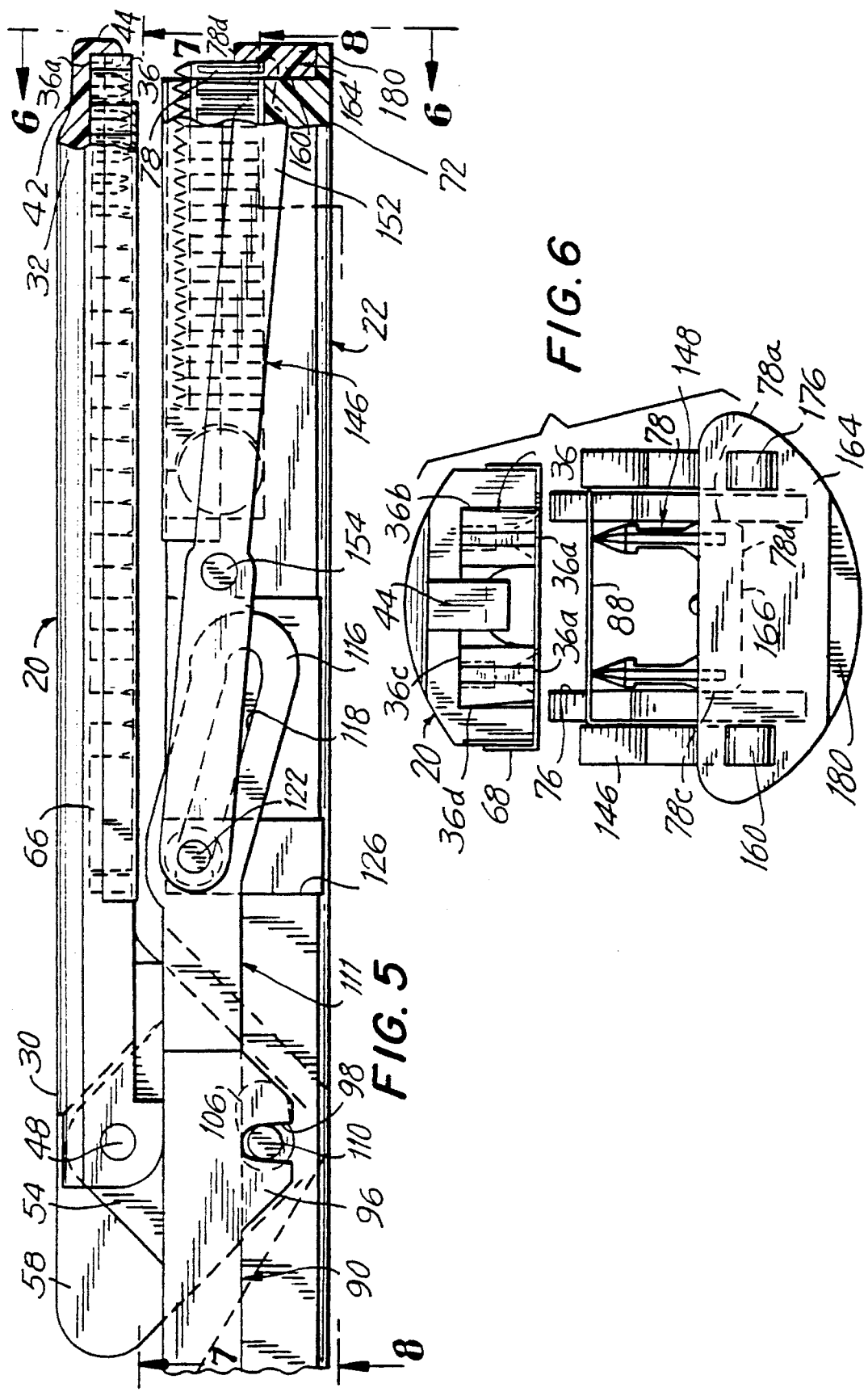

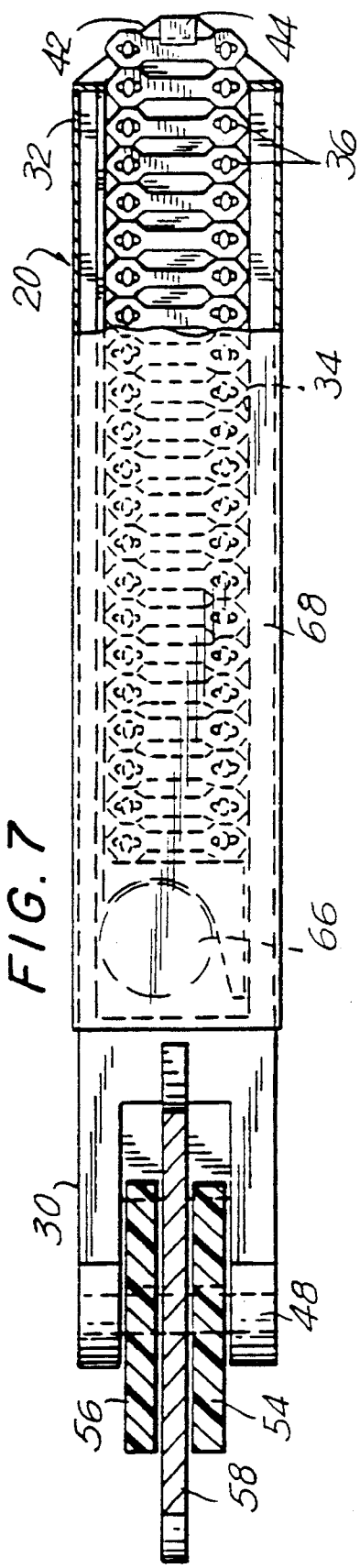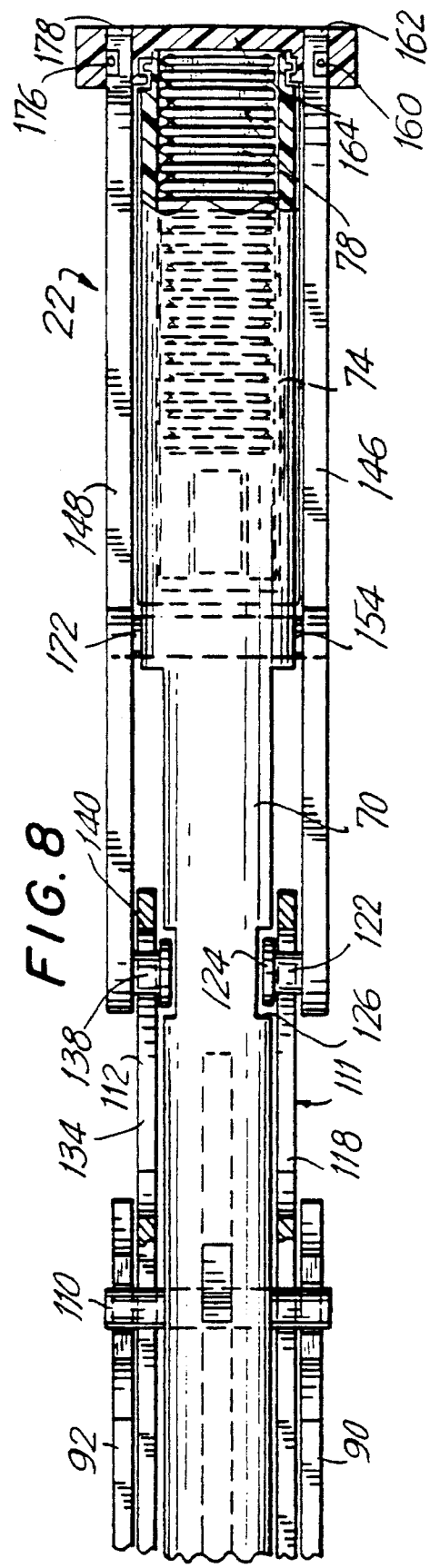
FIG. 7
FIG. 8

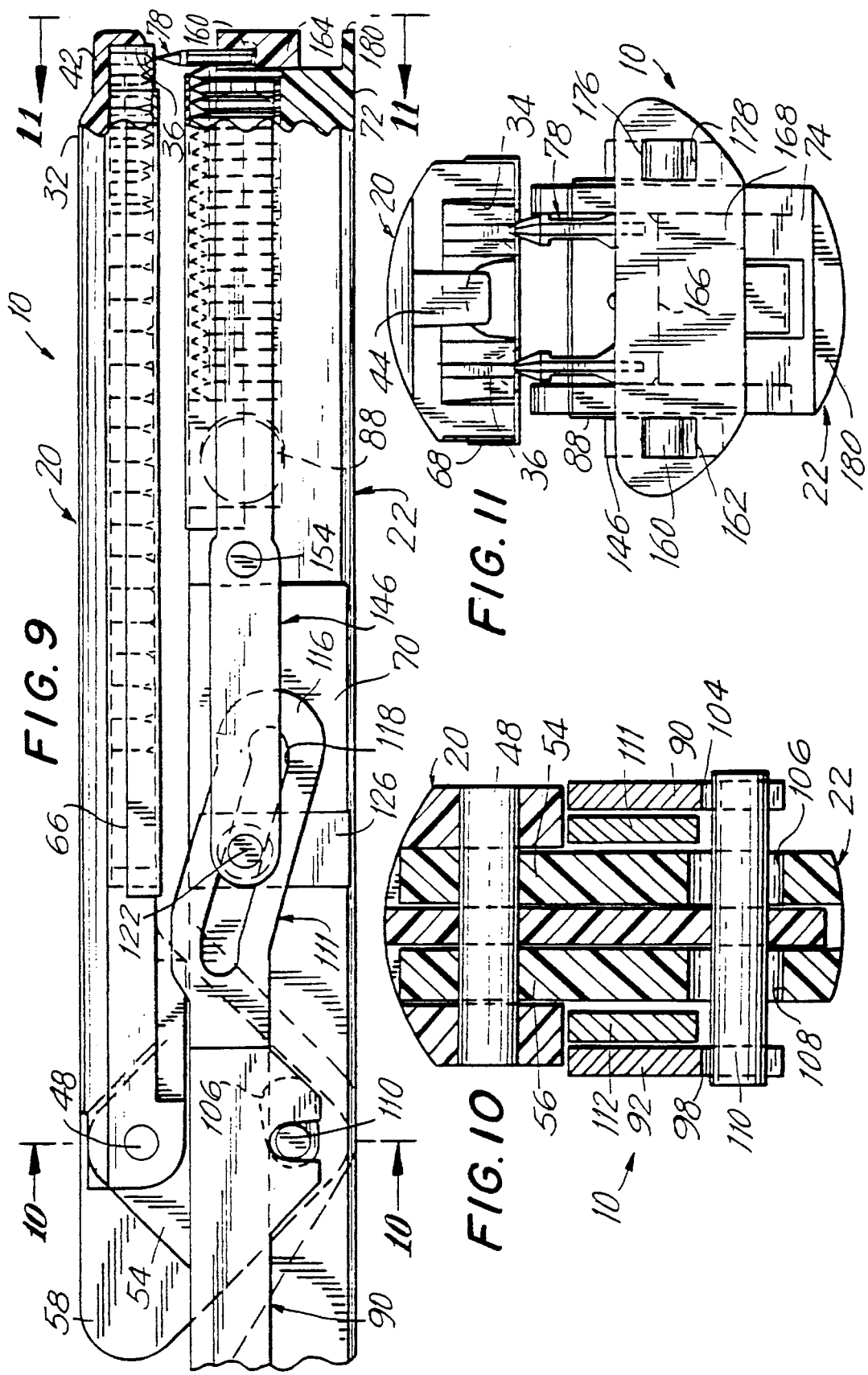

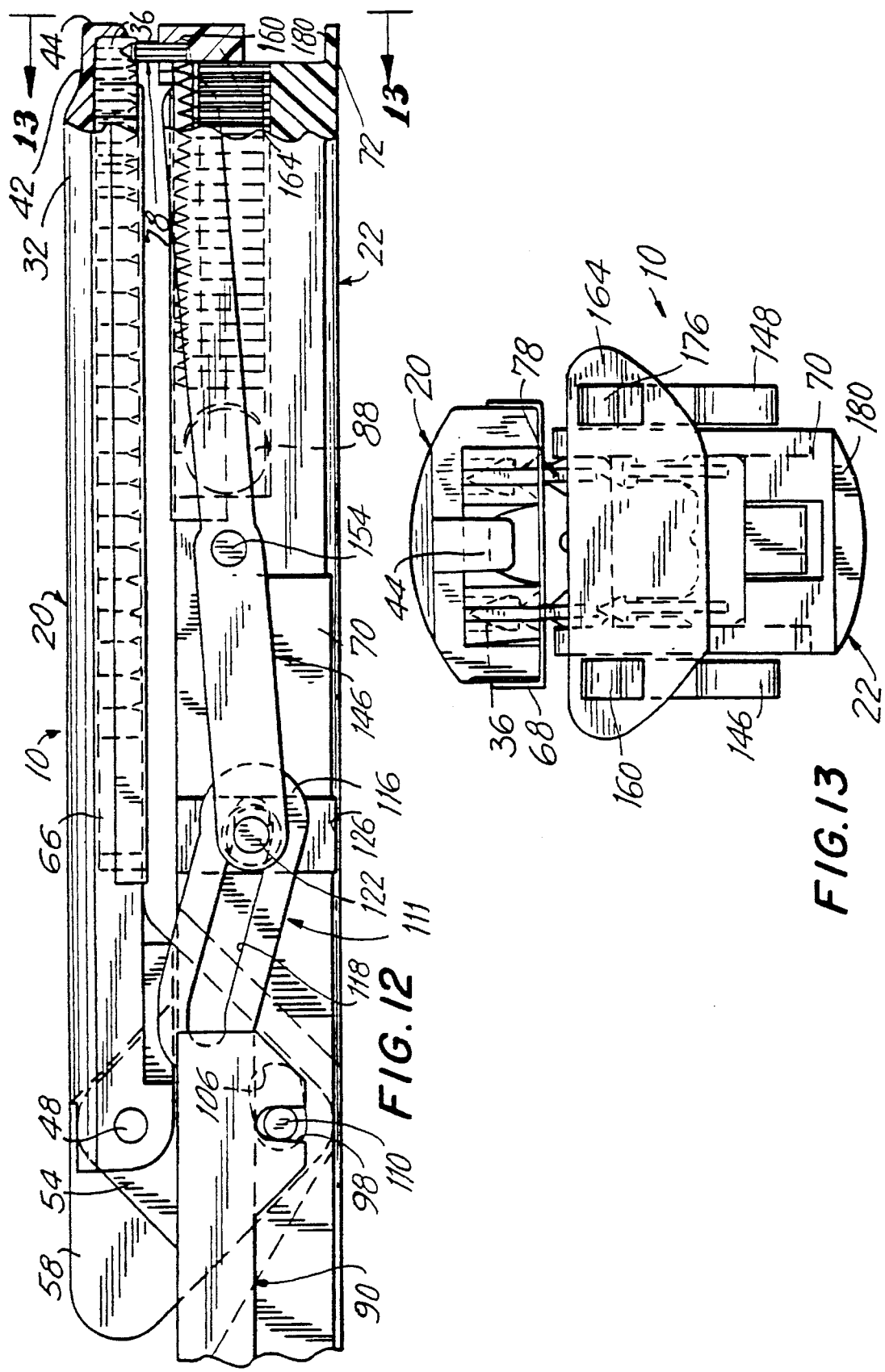

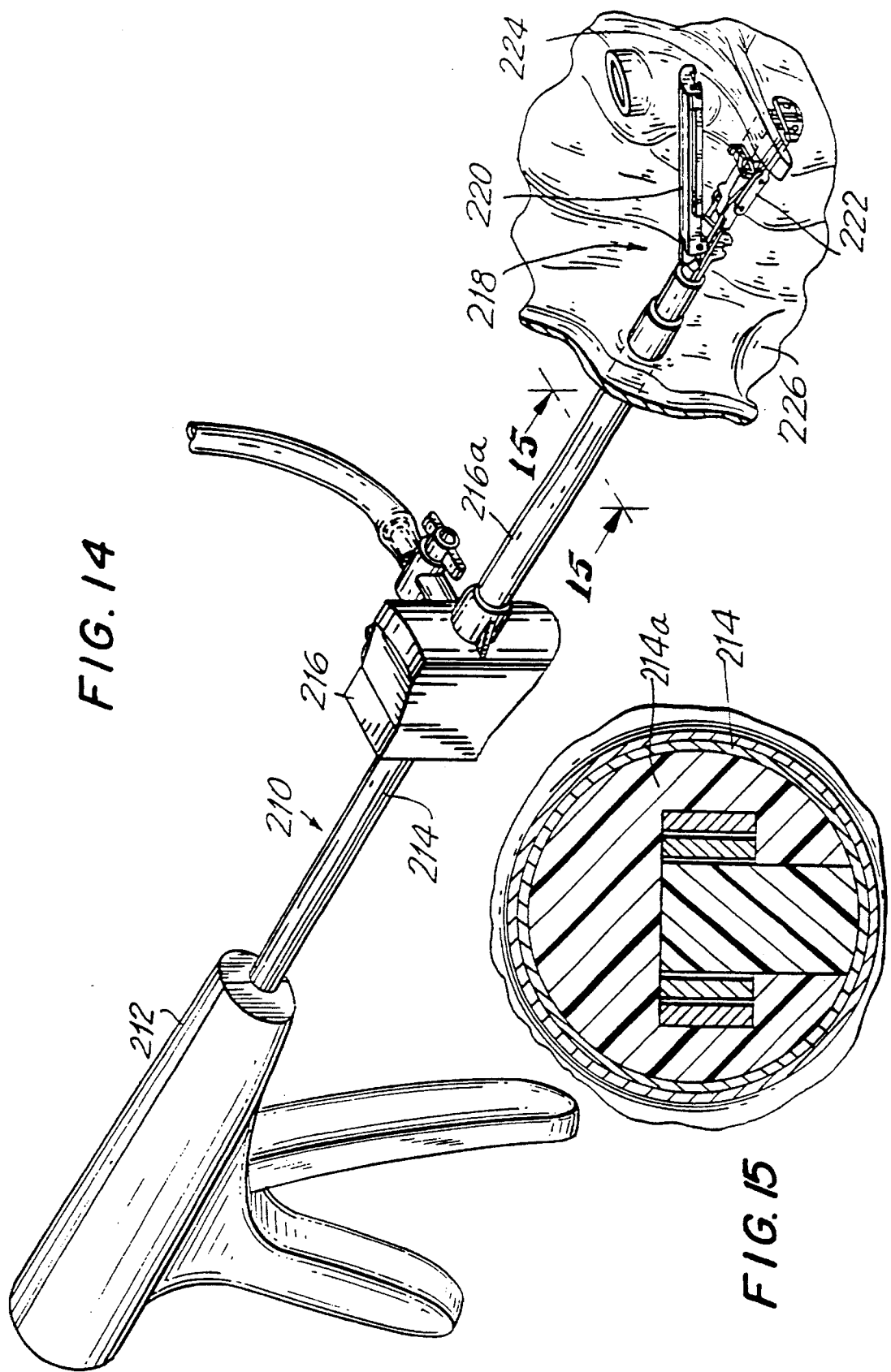

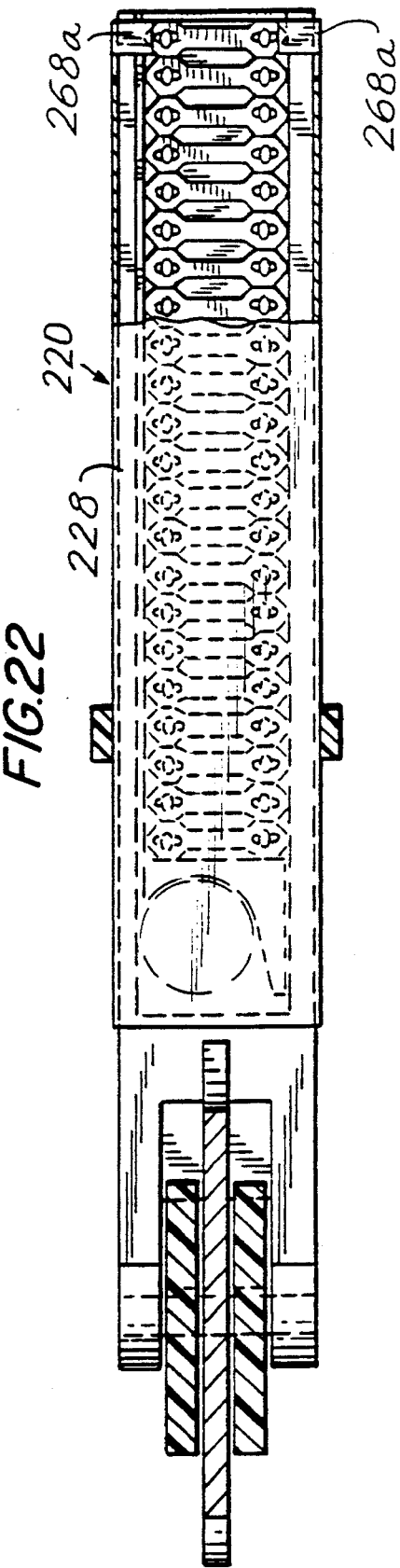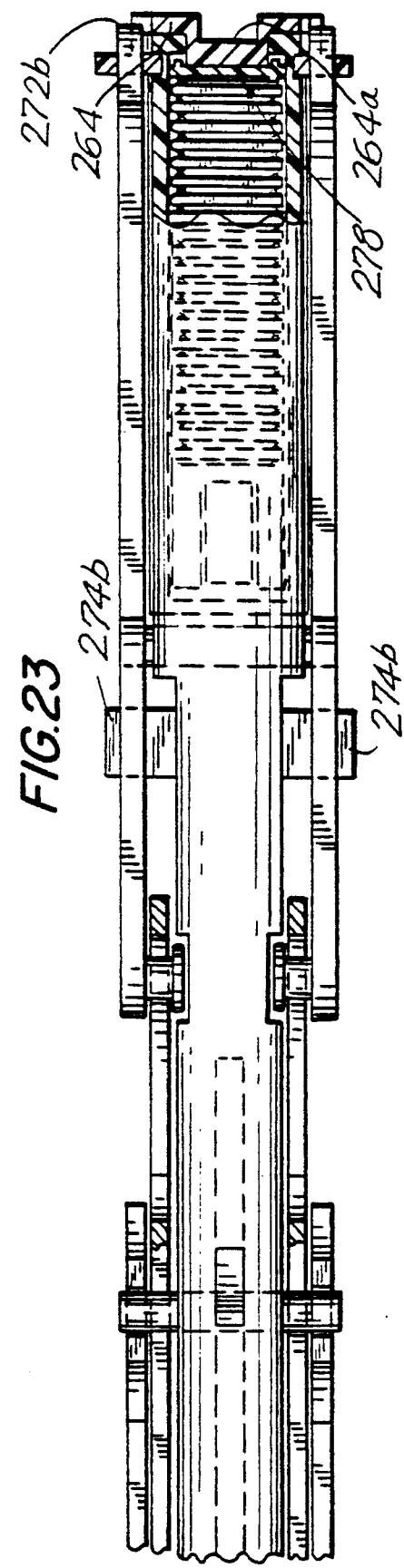
FIG.22
FIG.23

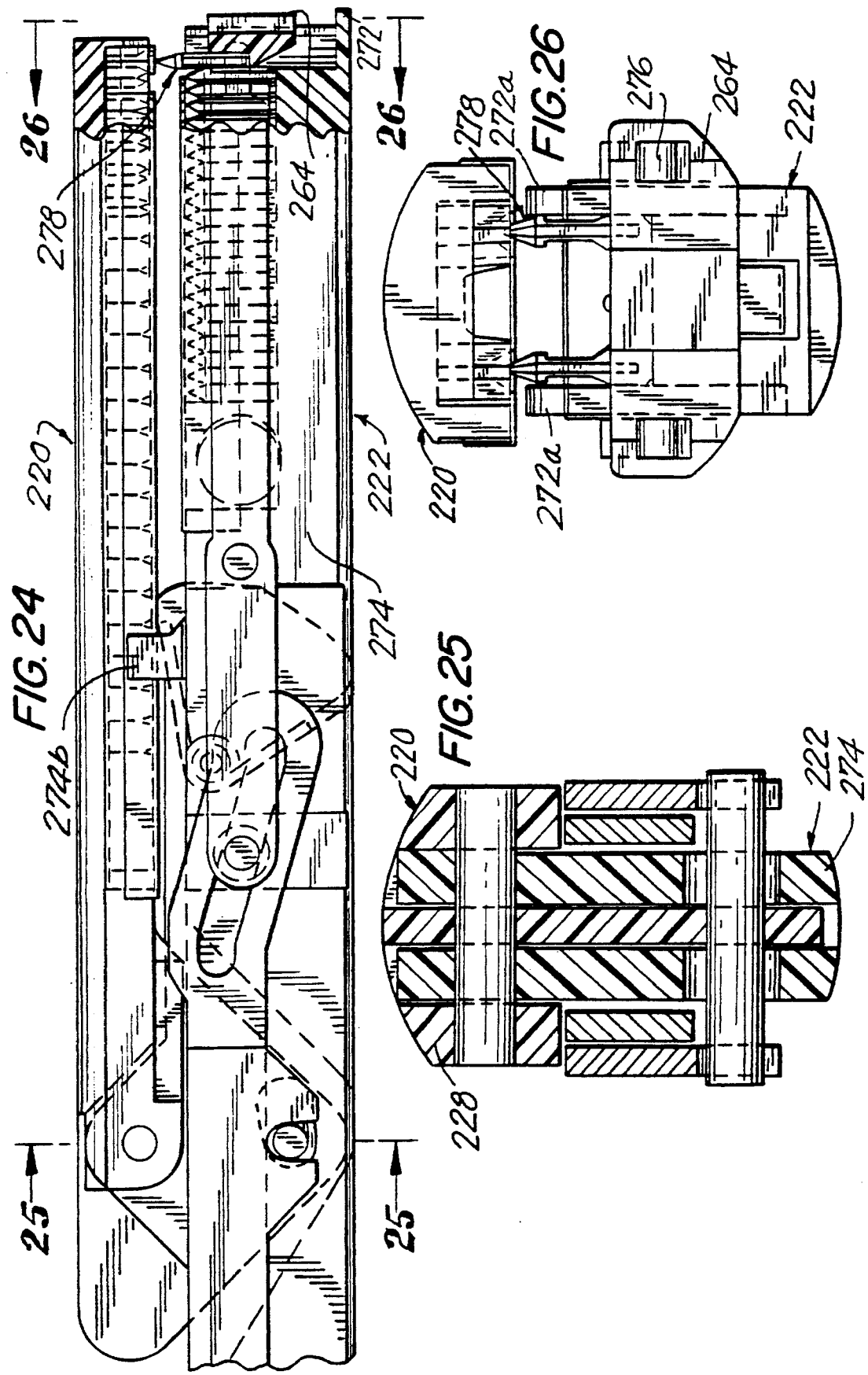

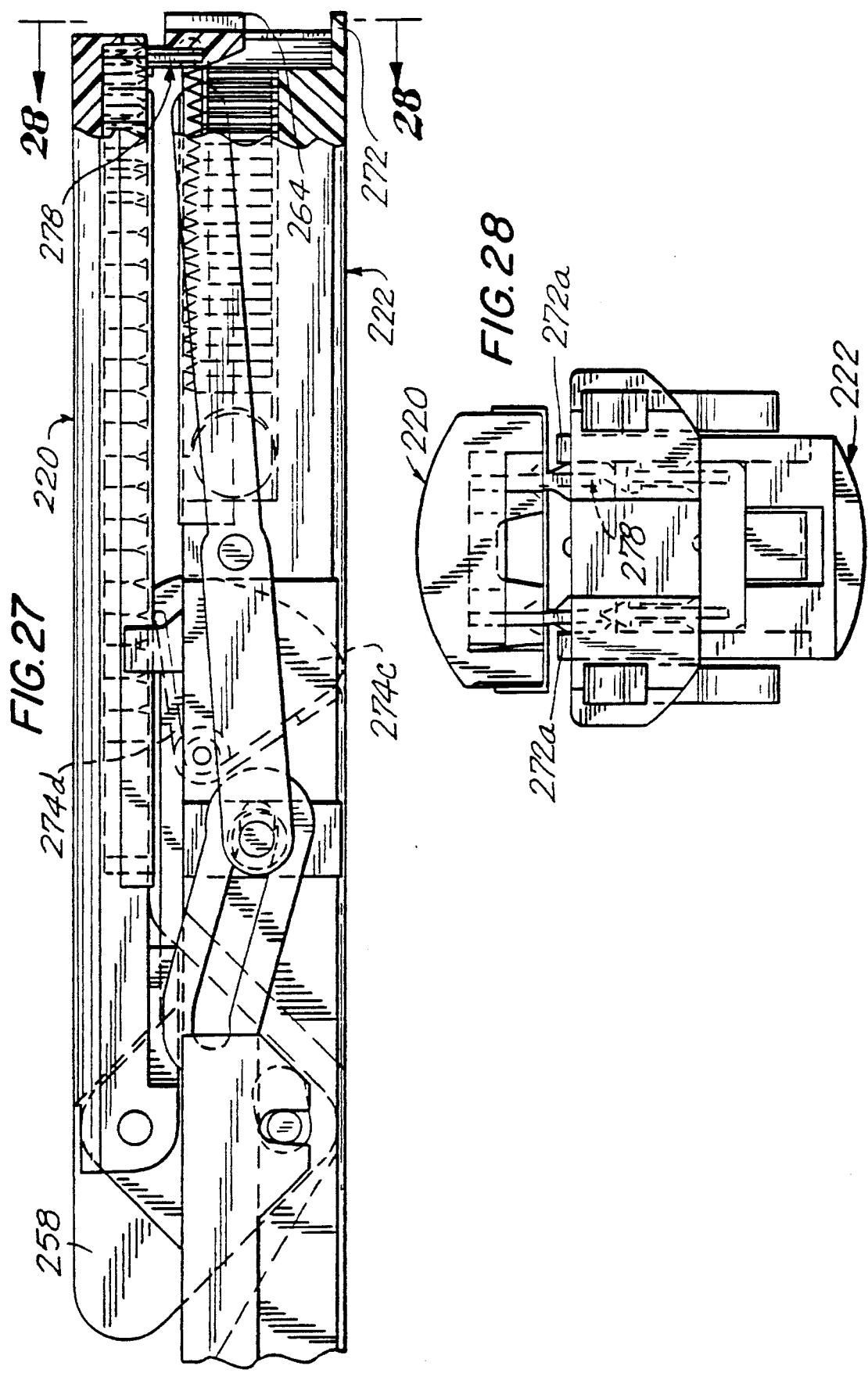

APPARATUS FOR APPLYING TWO-PART SURGICAL FASTENERS IN LAPAROSCOPIC OR ENDOSCOPIC PROCEDURES

This is a continuation of application Ser. No. 07/955,828 filed on Oct. 2, 1992, now abandoned.

BACKGROUND OF THE INVENTION

1. Field of the Invention

This invention relates to apparatus for applying surgical fasteners, and more particularly to a surgical apparatus for applying a two-part surgical fastener during endoscopic or laparoscopic procedures.

2. Background of Related Art

In laparoscopic and endoscopic surgical procedures, surgery is performed through a small incision or puncture made in the patient's body to provide access for an endoscopic tube or cannula device. Once extended into the patient's body, the cannula allows insertion of surgical instruments into the abdominal cavity. One such instrument is an apparatus for applying one or more surgical staples endoscopically as disclosed in U.S. Pat. No. 5,040,715 which issued to Green et al. This apparatus makes a longitudinal incision while simultaneously applying at least one row of staples on each side of the incision.

Up to the present, many devices for endoscopically applying fasteners have contemplated metal staples. It is advantageous however, to have the ability to apply a two-part non-metallic surgical fastener during such endoscopic procedures. Two-part absorbable fasteners are disclosed in U.S. Pat. Nos. 4,534,352, 4,589,416, 4,665,916 and 4,932,960. These fasteners include a fastener member which pierces the tissue from one side and a retainer which interlocks with the fastener member on the other side of the tissue. Subsequent to their application, the fasteners are advantageously absorbed by the body.

The present invention provides an apparatus for individually applying two-part surgical fasteners in endoscopic or laparoscopic procedures.

SUMMARY OF THE INVENTION

In accordance with the subject invention, a surgical apparatus is disclosed for placing at least one two-part surgical fastener endoscopically. The apparatus comprises activating means, an endoscopic portion which extends from the handle means, and means associated with a distal end of the endoscopic portion for applying a two-part surgical fastener. The activating means may be either a hand operated or a powered handle. Further, the apparatus preferably includes sealing means within the endoscopic portion to maintain positive pressure at the surgical site.

Preferably, the apparatus includes means for supporting a fastener portion of the surgical fastener, and means for supporting the retainer portion of the two-part surgical fastener in a position relative to the fastener portion thereof. The apparatus comprises means for approximating the retainer portion supporting means toward the fastener portion supporting means. Furthermore, the fastener applying means comprises means for driving the fastener portion of the two-part surgical fastener into engagement with the retainer portion of the two-part surgical fastener.

In a preferred embodiment, the retainer portion supporting means comprises an upper driving arm having a channel formed therein for maintaining and locating at least one retainer portion, while the fastener portion supporting means comprises a lower driving arm having a channel formed therein for maintaining and locating at least one fastener portion. The driving means is connected to the handle means and includes camming means and associated pivoting means. The camming means comprises at least one cam member having an angled head portion with an elongated cam slot defined therein. The pivoting means comprises at least one elongated rocker member pivotably connected intermediate the length thereof to the lower driving arm. The rocker member includes means for lifting a fastener portion of a two-part surgical fastener, and further comprises a cam follower for translation within the camming slot of the cam member. Preferably, the lifting means has a shelf defined therein for accommodating and retaining the fastener portion. The lifting means may be independently movable transversely of the endoscopic portion or it may be movably supported on rails associated with the endoscopic portion.

In a preferred embodiment, the approximating means is operatively connected to the handle means and includes at least one actuating member which may be an elongated draw bar, rod, or cable operatively connected to the upper driving arm, a clearance groove formed in a portion of the lower driving arm, and a camming pin connecting the draw bar to the upper driving arm through the clearance groove.

Further features of the subject invention will become more apparent from the following description of the subject invention.

BRIEF DESCRIPTIONS OF THE DRAWINGS

Preferred embodiments of the invention will be described hereinbelow with reference to the drawings wherein:

FIG. 1A is a cross-sectional view taken along lines 1A—1A of FIG. 1 illustrating the sealing means which allows the surgical site to be maintained at positive pressure;

FIG. 4 is a side elevational view of the apparatus of FIG. 1 with the retainer supporting portion in the open position;

FIG. 5 is a side elevational view of the apparatus of FIG. 1 with the retainer supporting portion in the closed position;

FIG. 6 is a front elevational view taken along lines 6—6 of FIG. 5;

FIG. 7 is a view, partially in cross-section, taken along lines 7—7 of FIG. 5 illustrating the retainer supporting portion of the apparatus of FIG. 1;

FIG. 8 is a view, partially in cross-section, taken along lines 8—8 of FIG. 5 illustrating the fastener supporting portion of the apparatus of FIG. 1;

FIG. 9 is a side elevational view of the apparatus of FIG. 1 with the retainer supporting portion in the closed position and further illustrating initial advancement of the distalmost fastener toward the corresponding distalmost retainer;

FIG. 10 is a cross-sectional view taken along lines 10—10 of FIG. 9;

FIG. 11 is a front elevational view taken along lines 11—11 of FIG. 9;

FIG. 12 is a side elevational view of the apparatus with the retainer supporting portion in the closed position and showing the distalmost fastener during insertion into the corresponding distalmost retainer;

FIG. 13 is a front elevational view taken along lines 13—13 of FIG. 12;

FIG. 14 is a perspective view of an alternative embodiment of the apparatus of the invention;

FIG. 15 is a cross-sectional view taken along lines 15—15 of FIG. 14 illustrating the sealing means which allows the surgical site to be maintained at positive pressure;

FIG. 22 is a view, partially in cross-section, taken along lines 22—22 of FIG. 19, illustrating the retainer supporting portion of the apparatus of FIG. 14;

FIG. 23 is a view, partially in cross-section, taken along lines 23—23 of FIG. 19, illustrating the fastener supporting portion of the apparatus of FIG. 14;

FIG. 24 is a side elevational view of the apparatus of FIG. 14, with the retainer supporting portion in the closed position and further illustrating initial advancement of the distalmost fastener toward the corresponding distalmost retainer;

FIG. 25 is a cross-sectional view taken along lines 25—25 of FIG. 24;

FIG. 26 is a front elevational view taken along lines 26—26 of FIG. 24;

FIG. 27 is a side elevational view of the apparatus of FIG. 14 with the retainer supporting portion in the closed position and showing the distalmost fastener during insertion into the corresponding distalmost retainer; and FIG. 28 is a front elevational view of the apparatus taken along lines 28—28 of FIG. 27.

DETAILED DESCRIPTION OF THE PREFERRED EMBODIMENTS

Figure 1:
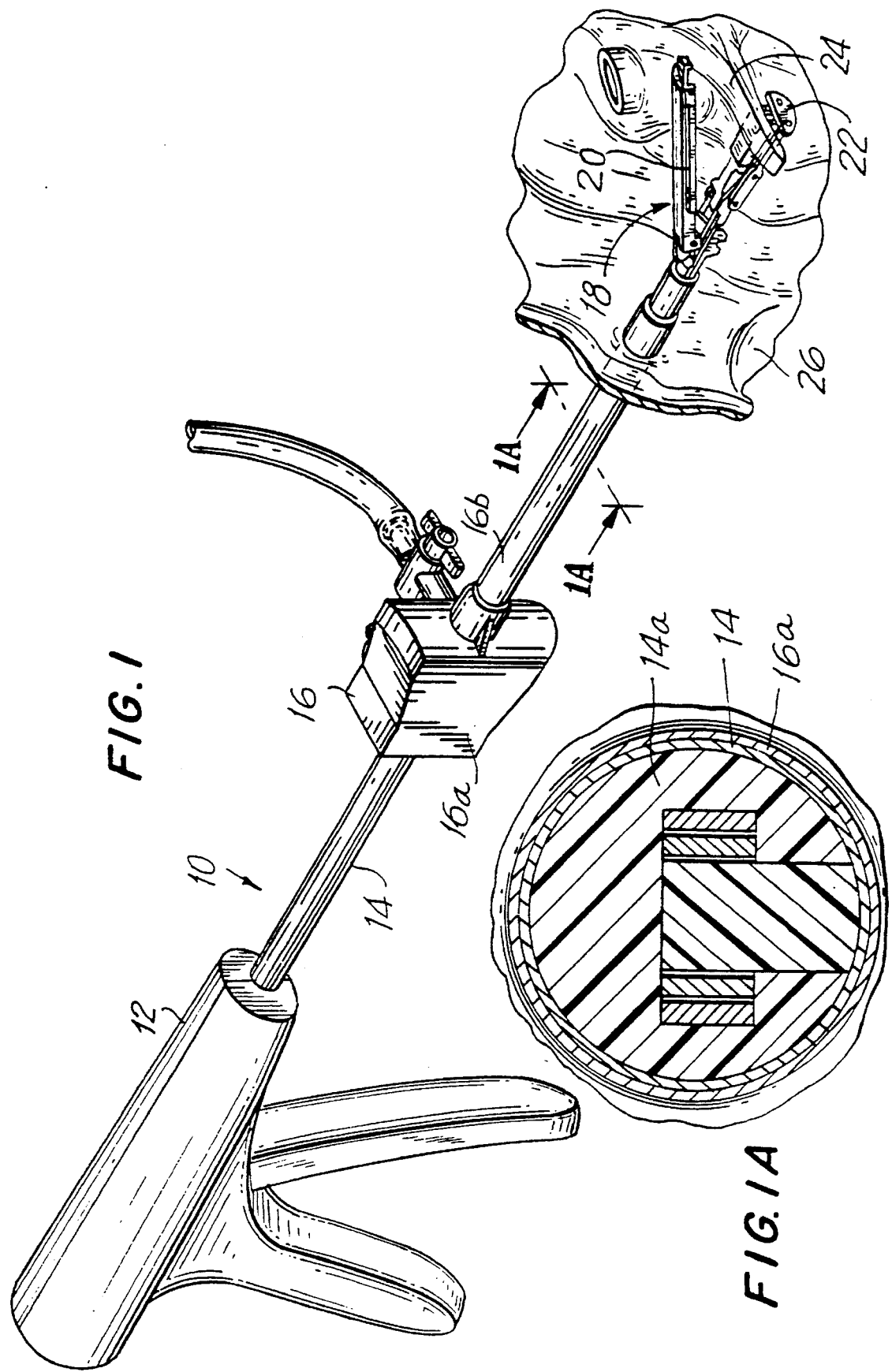
FIG. 1 is a perspective view of the apparatus for endoscopic application of two-part surgical fasteners in accordance with the subject invention.

The surgical apparatus of the subject invention is illustrated in FIG. 1 and is designated generally by reference numeral 10. Apparatus 10 basically comprises a handle portion 12, an elongated endoscopic portion 14 adapted for passage through a cannula assembly 16 having cannula housing 16a and cannula tube 16b and a fastener applying assembly 18 having a pair of cooperating arms 20 and 22 for applying a two-part surgical fastener to body tissue 24 within a body cavity 26 of a patient.

The preferred two-part surgical fastener is composed of a bioabsorbable polymeric material. Both bioabsorbable and non-bioabsorbable materials can be utilized. Examples of bioabsorbable material include homopolymers or copolymers of lactide, glycolide, polydioxanone, trimethylene carbonate, polyethylene oxide or other bioabsorbable polymer materials or blends of these respective copolymers. One preferred material is made of a copolymer of lactide and glycolide made from approximately 25% m glycolide and 75% m lactide blended with a homopolymer of glycolide so the total composition is composed of approximately 42% glycolide. Other bioabsorbable resinous materials for constructing such fasteners are disclosed in U.S. Pat. Nos. 4,523,591 and 4,744,365 to Kaplan et al., both of which are herein incorporated by reference. Clearly, other bioabsorbable materials can be utilized. Non-bioabsorbable materials contemplated include any implantable material such as polyester, polypropylene, or polyethylene.

Figure 2:
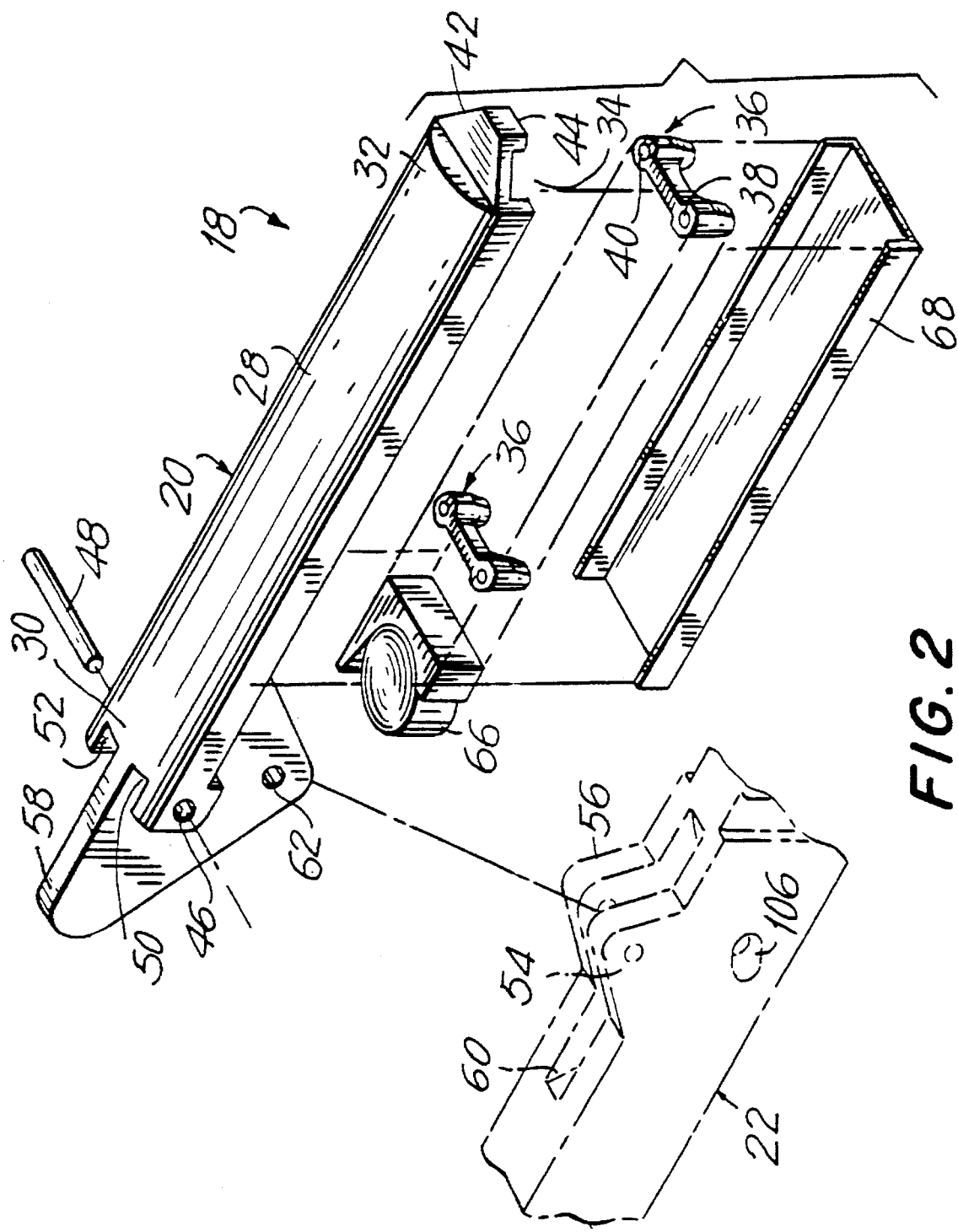
FIG. 2 is a perspective view with parts separated for convenience of illustration, of the fastener supporting portion of the apparatus of FIG. 1.

Referring now to FIGS. 2 and 7, the upper arm 20 of fastener applying assembly 18 has an elongated retainer supporting portion 28 having opposed proximal and distal ends 30 and 32. A substantially rectangular channel 34 is formed within the retainer supporting portion 28 for maintaining and feeding a plurality of retainers 36 which make-up half of the two-part surgical fastener which the apparatus 10 of the subject invention is designed to apply. The rectangular channel is configured and dimensioned to support, contain and feed retainers in the longitudinal direction along the channel. This is accomplished through the justification of the four outside surfaces 36a, 36b, 36c and 36d as shown in FIGS. 5 and 6. Each of the retainers 36 have spaced apart apertures 38 and 40 structured for engaged reception of the corresponding pronged legs of the fastener. A securement portion 42 with a down-turned lip 44 extends outwardly from the distal end 32 of the retainer supporting portion 28 of upper arm 20 for stabilizing the distalmost retainer 36 as well as locating the retainer relative to the distalmost fastener member. A mounting aperture 46 is provided in the proximal end 30 of retainer supporting portion 28 of arm 20 for receiving a pivot pin 48. Insert grooves 50 and 52 are defined in the proximal end 30 of retainer supporting portion 28 for cooperating with corresponding upstanding mounting struts 54 and 56 formed on the lower driving arm 22.

Figure 3:
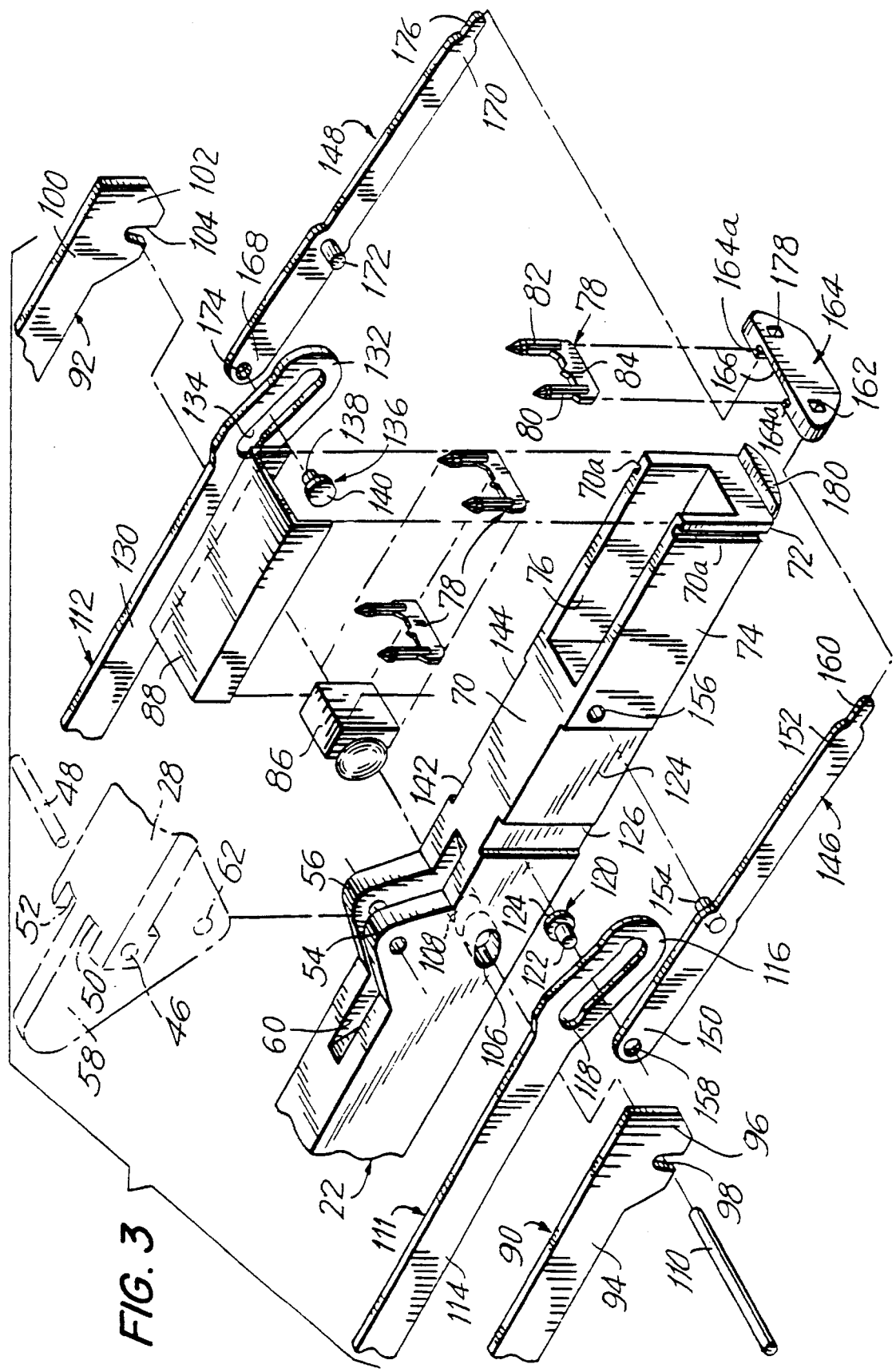
FIG. 3 is a perspective view with parts separated for convenience of illustration, of the retainer supporting portion of the apparatus of FIG. 1.

As shown in FIGS. 3 and 5, guide flange 58 extends from the proximal end 30 of retainer supporting portion 28 for cooperating with a longitudinal guide slot 60 formed in lower driving arm 22. An aperture 62 is provided in guide flange 58 for permitting cooperation of the upper arm 20 and the lower arm 22. This cooperation will be discussed further hereinbelow. A spring loaded biasing member 66 is disposed within the rectangular channel 34 of retainer supporting portion 28 for biasing a plurality of retainers members 36 toward the distal end 32 of retainer supporting portion 28. Biasing system 66 is adapted for uniform plunger-like translation along the longitudinal axis of the elongated driving arm 20 within channel 34 and operates through a coiled spring mechanism (shown schematically) to bias the retainers in the distal direction. An elongated cover plate 68 is provided for mounting to the retainer supporting portion 28 of arm 20 adjacent channel 34 for maintaining the retainer 36 and the biasing member 66 in channel 34.

Referring to FIGS. 3 and 8, the lower driving arm 20 of the surgical fastener applying assembly 18 includes a body portion 70 having a distal end 72. A fastener supporting portion 74 is defined adjacent the distal end 72 of body portion 70 and is provided with a substantially rectangular channel 76 for maintaining and feeding a plurality of fastener members 78 which make-up the second half of the two-part surgical fastener contemplated for application by the apparatus 10 of the subject invention. The rectangular channel is configured and dimensioned to support, contain and feed subsequent fastener members along the longitudinal axis of the channel. This is accomplished through the justification of the four outside surfaces 78a (side), 78b (bottom), 78c (side) and 78d (distal) of the fastener members as best shown in FIGS. 5 and 6. Each of the fastener members 78 include two prongs 80 and 82 extending from a backspan 84. Prongs 80 and 82 are adapted for engagement within the spaced apart aperture areas 38 and 40 of retainer 36. A biasing member 86 is disposed within the proximal end of channel 76 for uniformly urging the plurality of fastener portions 78 in plunger-like fashion toward the distal end 72 of body portion 70 and operates through a known coiled spring mechanism, the details of which are not shown. An elongated cover member 88 is provided for mounting adjacent channel 76 so as to maintain fasteners 78 and biasing member 86 within channel 76.

The surgical apparatus 10 further comprises a mechanism for approximating the upper arm 20 toward the lower arm 22 during surgical procedures. The approximating mechanism comprises a pair of elongated draw bars 90 and 92 which are disposed on either side of lower arm 22 and operatively connected to the handle portion 12 through endoscopic portion 14. Draw bar 90 has an elongated body portion 94 and a distal head portion 96 depending from body portion 94 which is provided with an inverted U-shaped notch 98. Similarly, draw bar 92 has an elongated body portion 100 having a distal head portion 102 which depends therefrom and which is provided with an inverted U-shaped notch 104. The approximating mechanism further includes a pair of opposed clearance grooves 106 and 108 which are defined in the body portion 70 of lower arm 22. Clearance grooves 106 and 108 each approximately describe an arc whose center of rotation is the pivot 48 of upper arm 20. An elongated pin 110 extends through clearance grooves 106 and 108 and aperture 62 in the guide flange of upper arm 20, and is engaged in the inverted U-shaped notches 98 and 104 in draw bars 90 and 92, respectively. Longitudinal movement of draw bars 90 and 92 will cause corresponding translation of the pin 110 within clearance grooves 106 and 108. This movement causes corresponding approximating movement of the upper arm 20 relative to the lower arm 22.

With continued reference to FIG. 3, the surgical apparatus 10 of the subject invention further includes a mechanism for driving at least one of the plurality of fastener members 78 into engagement with at least one of the retainers 36 of the two-part surgical fastener, for fastening tissue during a surgical procedure. It is envisioned however, that this mechanism may be configured in such a manner so as to simultaneously drive a predetermined number of fastener members 78 into engagement with a predetermined number of retainers 36. The driving mechanism comprises a linkage assembly including a pair of elongated camming arms 111 and 112 disposed on either side of the body portion 70 of lower arm 22. Camming arms 111 and 112 are operatively connected to the handle portion 12 of the apparatus 10 through endoscopic portion 14. Camming arm 111 includes an elongated body portion 114 and a head portion 116 which depends angularly from the elongated body portion 114. A camming slot 118 is defined in the head portion 116 for accommodating translation of the camming arm 111 relative to a cam follower 120. More particularly, the cam follower 120 has a head portion 122 which cooperates with the cam slot 118, and a tail portion 124 adapted for linear movement within a transverse clearance track 126 formed in side wall 128 of body portion 70.

Similarly, camming arm 112 has an elongated body portion 130 and a head portion 132 which depends angularly from the body portion 130. A camming slot 134 is defined in the head portion 132 for permitting translation of camming arm 112 relative to a cam follower 136 having a head portion 138 which cooperates with camming slot 134, and a tail portion 140 adapted for linear movement within a transverse clearance track 142 formed in side wall 144 of body portion 70. The driving mechanism further comprises a pair of elongated pivoting rocker arms 146 and 148. Rocker arm 146 has opposed proximal and distal ends 150 and 152 and is pivotably connected to the body portion 70 of lower driving arm 22 by an integral pivot pin 154 which is mountable within an aperture 156 provided in body portion 70. An aperture 158 is provided at the proximal end 150 of rocker arm 146 for engagement with the head portion 122 of cam follower 120. This connection, links the rocker arm 146 with the camming arm 111. An outwardly extending prong 160 is provided at the distal end 152 of rocker arm 146. Prong 160 is engagable within a receiving aperture 162 formed in a lift member 164.

As shown in FIG. 3, lift member 164 is provided with inwardly extending rails 164a which are slidable for up and down movement within grooves 70a in body portion 70. The rails 164a and grooves 70a facilitate steady upward and downward movement for lift member 164 to provide accurate alignment of fastener member 78 with corresponding retainer 36 as will be described.

As shown in FIG. 4, lift member 164 has a groove 166 formed therein (see also FIG. 11) for receiving and locating the distalmost fastener member 78 from channel 76 relative to the distalmost retainer. This groove also retains the distalmost fastener member and prevents longitudinal and lateral motion during its insertion into the retainer. Rocker arm 148 has opposed proximal and distal ends 168 and 170 and is pivotably mounted to body portion 70 of lower driving arm 22 by an integral pivot pin 172 disposed intermediate proximal and distal ends 168 and 170 thereof. An aperture 174 is provided in the proximal end 168 of rocker arm 148 for engaging the head portion 138 of cam follower 136 to interconnect rocker arm 148 with camming arm 112. A prong 176 extends outwardly from the distal end 170 of rocker arm 148 for engagement in a receiving aperture 178 provided in lift member 164. A positioning stop 180 extends outwardly from the distal end 72 of body portion 70 for locating the lift member 164 of the driving mechanism.

In operation, once the fastener applying assembly 18 of the surgical apparatus 10 of the subject invention has been extended into the body cavity 26 as illustrated in FIG. 1, the upper arm 20 of assembly 18 may be moved into an open position, best seen in FIG. 4. In this open position, the elongated push rod 90 of the approximating mechanism is in its distalmost position resulting in the camming pin 110 being maintained in a distal area of the clearance groove 106. By maintaining the camming pin 110 in this manner, the upper arm 20 is supported in an upright position which is desirable to receive tissue between the cooperating arms 20 and 22 of the fastener applying assembly 18. Furthermore, when in this non-operative tissue receiving position, the fastener driving mechanism of the apparatus 10 is in a neutral condition wherein the angled head portion 116 of cam arm 11 is in its distalmost position. Consequently, the cam follower 120 is positioned in the most proximal area of the cam slot 118 of head portion 116, while at the same time being disposed in its highest position within the transverse clearance track 126 formed in body portion 70 of lower arm 22. Thereupon, the distal end 152 of the pivoting rocker arm 146 is in its lowest position at the distal end 72 of the lower arm 22. While in this lowest position, the lift member 164, which is secured to the prong 160 at the distal end 152 of rocker arm 146 is supported upon the positioning stop 180 which extends outwardly from the distal end 72 of body portion 70.

Turning to FIG. 5, once tissue has been disposed between the cooperating arms 20 and 22, the upper arm 20 may be approximated toward the lower arm 22, closing the gap therebetween, until such time as the axes of each arm are substantially parallel to one another thereby retaining the tissue therebetween. The approximation of arm 20 is achieved through manipulating the handle portion 12 of the apparatus 10 in such a manner so as to pull the elongated draw bar 90 in a proximal direction causing camming pin 110 to move into a proximal area of the angularly oriented clearance groove 106. Once arm 20 has been approximated, the distalmost retainer 36 of the two-part surgical fastener is in a position for receiving the distalmost fastener member 78 of the two-part surgical fastener, as best seen in FIGS. 6-8. More particularly, the backspan 84 of the distalmost fastener member 78 is supported and aligned within groove 166 formed in the lift member 164. At the same time, the distalmost retainer 36 is secured in a receiving position by the down-turned lip 44 of the securement portion 42 which is disposed at the distal end 32 of upper arm 20 (see FIG. 7).

As shown in FIG. 1A the distal portion of endoscopic portion 14 includes internal sealing means 14a which maintains the operative site at positive pressure during the endoscopic or laparoscopic surgical procedure. The sealing means is formed of a compliant impermeable material such as closed-cell foam rubber or natural or synthetic rubber, or a viscous liquid such as silicone grease, for example. The material surrounds the actuating members as shown in FIG. 1A within endoscopic tubular portion 14. Such compliant material forms a gasket seal around the actuating members while still permitting the longitudinal movement of the actuating members through the sealing means with no loss of insufflation pressure past the sealing means.

Referring now to FIGS. 9-11, the handle means 12 of the apparatus 10 may be manipulated in such a manner so as to drive the distalmost fastener member 78 toward the distalmost retainer 36 of the two-part surgical fastener. In driving a fastener member, the angled head portion 116 of cam arm 111 is moved in a proximal direction, relative to the cam follower 120. Concomitantly, cam follower 120 translates in a downward direction within the transverse clearance track 126 formed in body portion 70. As a consequence of the camming movement of cam follower 120, the distal end 152 of the rocker arm 146 is moved upwardly, carrying the lift member 164 off of positioning stop 180, and thereupon urging the fastener member 78 toward the retainer 36 of the two-part surgical fastener.

Turning now to FIGS. 12 and 13, to drive the distalmost fastener member 78 into engagement with the retainer 36, whereby the two prongs 80 and 82 at the end of backspan 84 will be interlocked within the spaced apart aperture areas 38 and 40 of the distalmost retainer 36, the camming arm 111 is moved in such a manner so that the cam follower 120 is positioned in the distalmost area of cam slot 118, and is moved into its lowest position in the transverse track 126 formed in body portion 70. Consequently, the distal end 152 of rocker arm 146 is pivoted into its highest position relative to lower driving arm 22, causing lift member 164 to urge the distalmost fastener member 78 into engagement with the distalmost retainer 36 of the two-part surgical fastener. As the distalmost fastener member 78 engages the distalmost retainer 36 it becomes applied to the target tissue. At this point, the distalmost fastener member 78 will have essentially exited the rectangular channel 76 and is essentially free of the grip of channel 76 of body portion 70. During this process while the lift member 164 is in the driving position, the body of the lift member withholds the line of fasteners from moving distally under the force of biasing member 86 which normally urges the line of fasteners in the distal direction. As lift member 164 returns to its home position toward positioning stop 180 the proximal wall 164a of lift member 164 engages the distally biased distalmost fastener and urges the entire row of fasteners to move proximally a small amount. When the lift member 164 returns to its home position on the positioning stop 180 by the reverse sequence of the mechanical operation described, the biasing member 86 in channel 76 of body portion 70 urges the next-in-line fastener member 78 into a driving position. The cooperating arms 20 and 22 of the fastener applying assembly 18 can then open. Since the distalmost fastener member 78 and the distalmost retainer 36 are now locked onto the target tissue, this opening motion will cause the distalmost retainer 36 to be withdrawn from the upper arm 20, passing over the down-turned lip 44. At this point the biasing member 66 in channel 34 of support portion 28 urges the next-in-line retainer 36 into position against the securement portion 42 with down-turned lip 44. This effectively completes the process and the instrument is now ready for the next application of surgical fasteners.

Referring now to FIG. 14 an alternative embodiment of the inventive apparatus is shown and is designated generally by reference numeral 210. In the description of this alternative embodiment which follows, like components are identified by similar numerals as like components are identified in the previous embodiment. In addition, certain components common to the previous embodiment are illustrated in the drawings but not identified by numerals since they are identical to the corresponding components previously described.

Referring again to FIG. 14, apparatus 210 includes handle portion 212, and elongated endoscopic portion 214 adapted for passage through cannula assembly 216 having cannula housing 216a and cannula tube 216b and including an internal seal 214a. Fastener applying assembly 218 at the distal end of endoscopic portion 214 includes a pair of cooperating arms 220 and 222 for applying a two-part surgical fastener on tissue 224 within the body cavity 226 of a patient. The structure and operative principles of the embodiment shown in FIG. 14 are identical in most respects to those of the previous embodiment with the exceptions specifically described in the description which follows.

Figure 16:
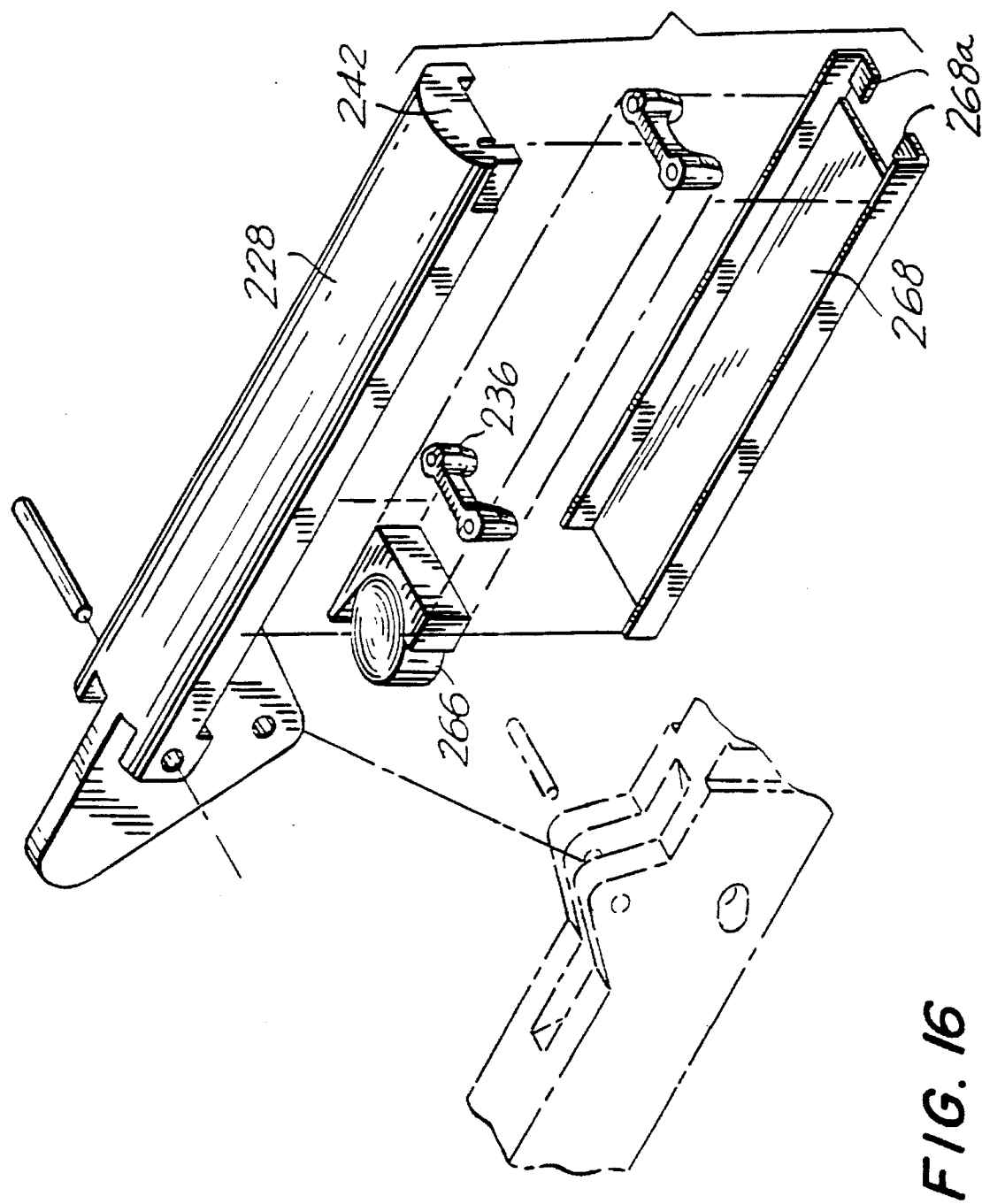
FIG. 16 is a perspective view with parts separated for convenience of illustration, of the retainer supporting portion of the apparatus of FIG. 15.
Figure 18:
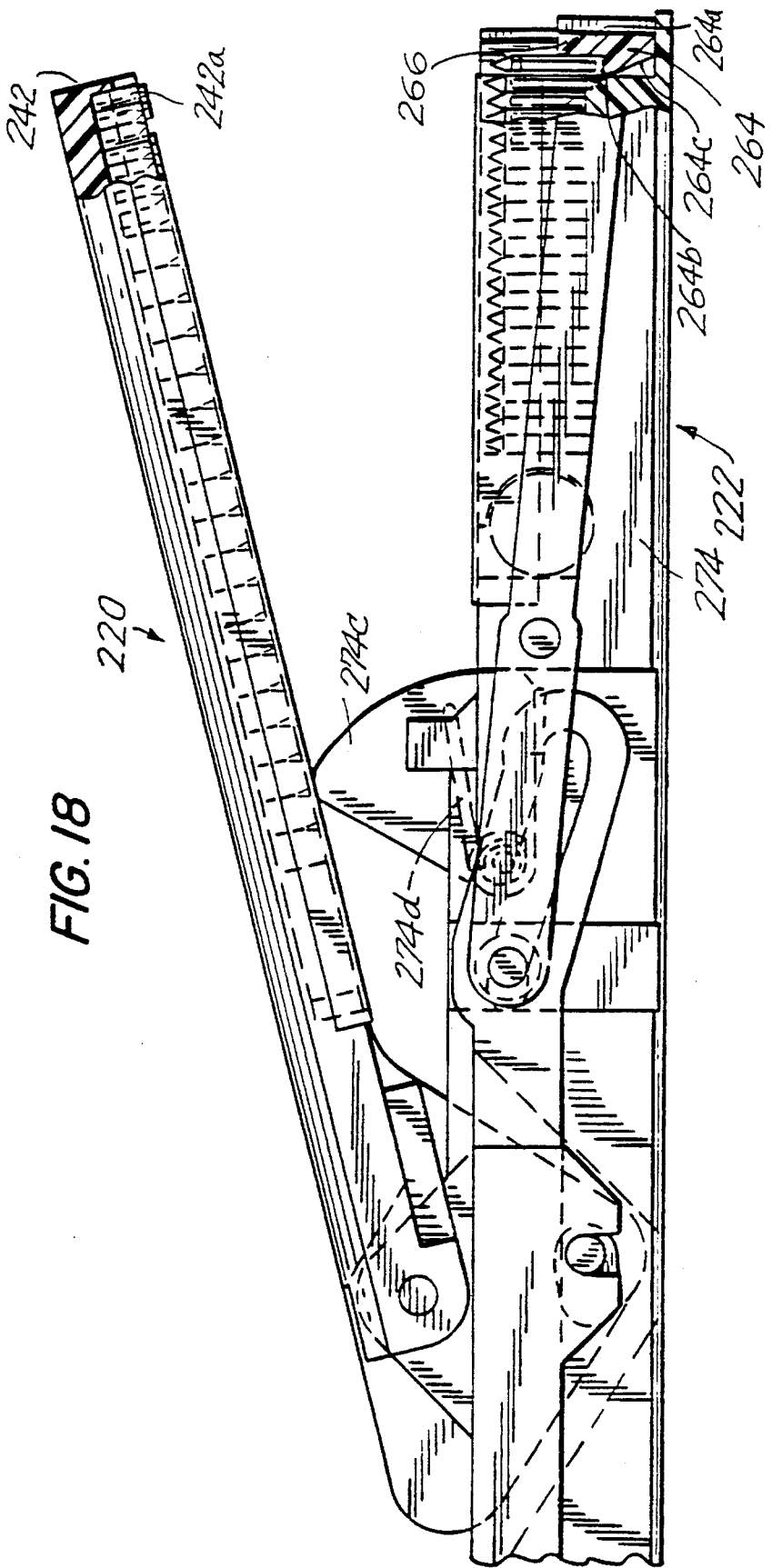
FIG. 18 is a side elevational view of the apparatus of FIG. 14 with the retainer supporting portion in the open position.

In FIG. 16, retainer supporting portion 228 is modified at the distal end by replacing securement portion 42 of the previous embodiment with distal wall 242 to receive and guide retainers 236 as best shown in FIG. 18. The flat inner surface 242a of distal wall 242 as best shown in FIG. 18 provides precise positioning of the distalmost retainer during advancement of the retainer 236. Additionally, the cover plate 268 incorporates two compliant fingers 268a which partially contain the distal-most retainer 236. After insertion of the fastener and opening of the retainer supporting portion 228, these compliant fingers 268a deflect allowing the withdrawal of the distalmost retainer. After insertion of fastener 218 into retainer 236, the retainer moves with the fastener and is thus released by compliant fingers 268a.

Figure 17:
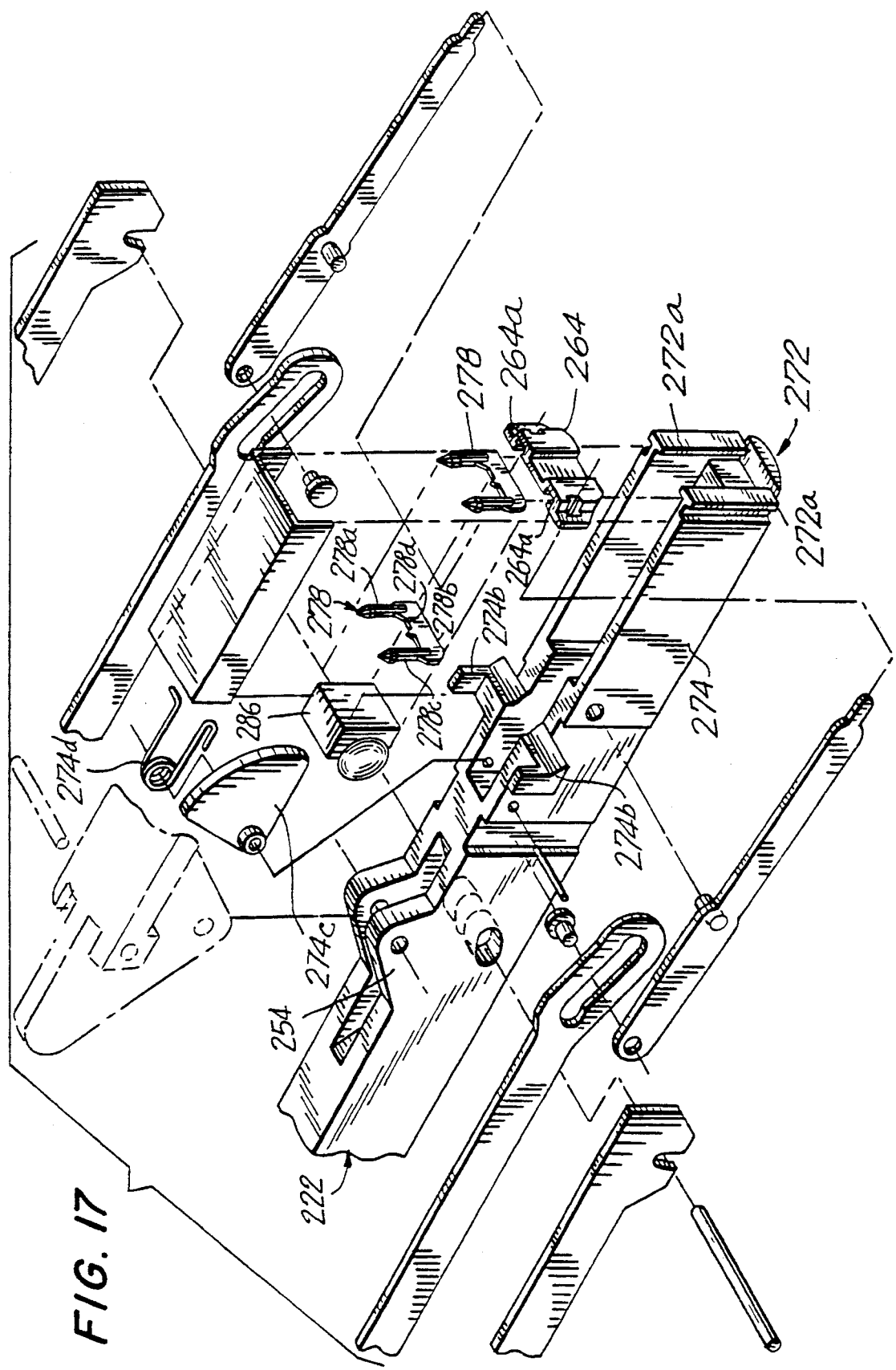
FIG. 17 is a perspective view with parts separated for convenience of illustration, of the fastener supporting portion of the apparatus of FIG. 14.
Figure 19:
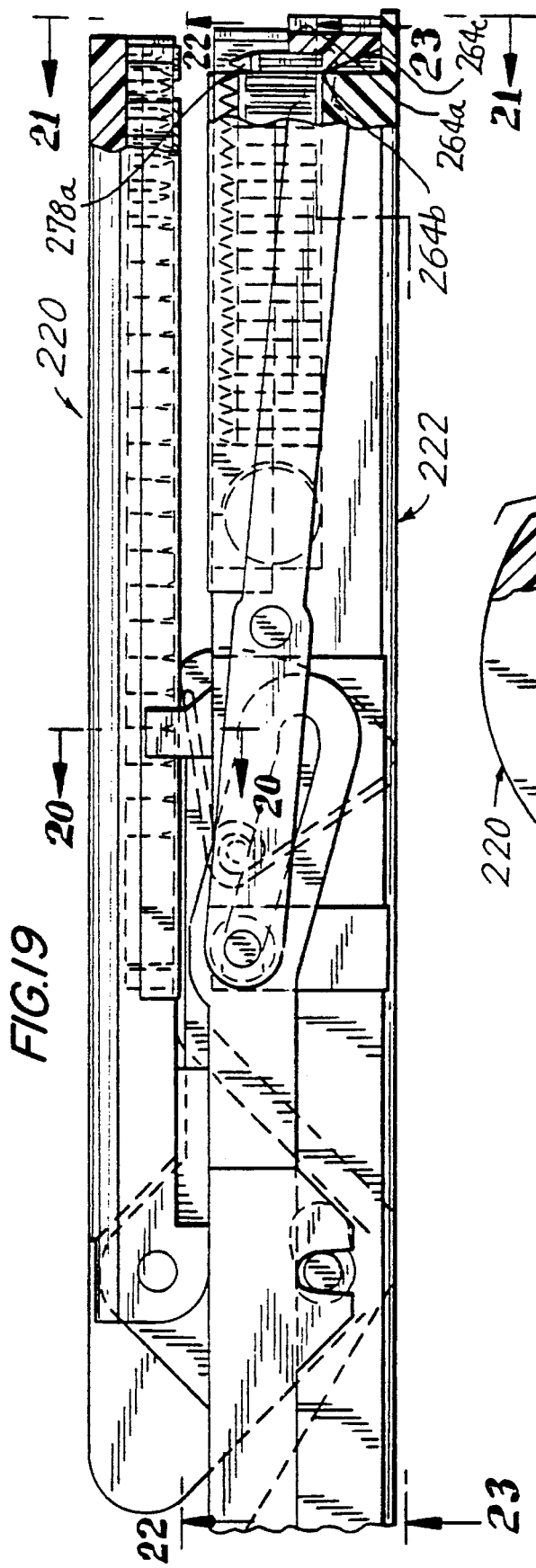
FIG. 19 is a side elevational view of the apparatus of FIG. 14 with the retainer supporting portion in the closed position.
Figure 21:
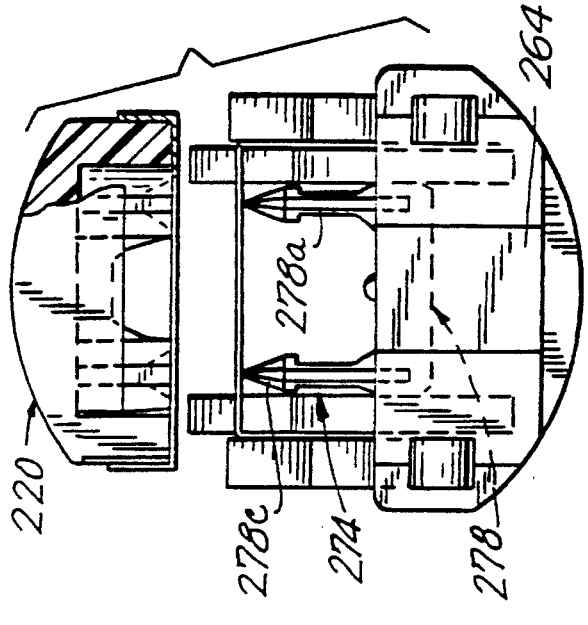
FIG. 21 is a front elevational view taken along lines 21—21 of FIG. 19.
Figure 20:
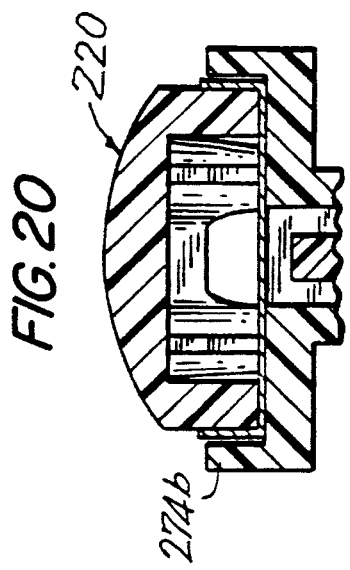
FIG. 20 is a cross-sectional view taken along lines 20—20 of FIG. 19.

Referring now to FIG. 17, the fastener supporting portion of the embodiment of FIG. 14 is illustrated. As noted, this embodiment includes components identical to the previous embodiment, except that lift member 164 of the previous embodiment has been replaced by lift member 264 which includes vertical channels 264a configured and dimensioned to slidably receive correspondingly configured and dimensioned rails 272a at the distal end 272 of fastener supporting portion 274. Thus the distalmost fastener 278 is protected and positively positioned in every significant coordinate surface for movement in directions toward and away from the retainer support means 228 of FIG. 16. As can be seen in FIG. 21 the bottom surface 278b is in surface contact with the lift member 264, side surfaces 278a and 278c are in contact with the side walls of lift member 264 and as shown in FIG. 19 the distal surface 278d is in contact with the proximal wall 264a of lift member 264. As seen in FIG. 23 the distal wall of fastener 278 is in positive contact with the proximal surface 272b of rails 272a of fastener support 274. As can be seen in FIG. 17, 19 and 23, when lift member 264 is in position at the distal end of support 274 a positive support surface for fastener 278 is provided by the proximal surface 264a of the lift member 264. This precise positioning of fastener member 278 thus facilitates precise interactive mating of the fastener members 278 and retainers 236 when the lift member 264 is advanced upwardly toward the retainer support means 228 as described in the previous embodiment as illustrated in FIGS. 24–28.

Referring now to FIG. 18 the lift member 264 in this embodiment is shown in cross-section and includes proximal groove 264d similar to the corresponding groove in lift member 164 described in connection with the previous embodiment. This groove is defined between proximal wall 264a and proximal lip 264b and is dimensioned and configured as shown to snugly maintain the precise positioning and orientation of fastener 278. Also, in this embodiment, lift member 264 is configured to include tapered proximal surface 264c as shown on the lower half portion. Thus during the fastener lifting process as described in connection with the previous embodiment, the tapered proximal surface 264c will initially permit the fasteners to move forward a slightly greater amount under bias of resilient member 286. Thereafter, as lift member 264 is lowered the gradual taper of proximal surface 264c will initially permit the fasteners to move forward a slightly greater amount under bias of resilient member 286. Thereafter, as lift member 264 is lowered the gradual taper of proximal surface 264c will contact the fastener next-in-line and provide a slight proximal movement to the row of fasteners as the lift member 264 returns to its home position below the next-in-line fastener. Essentially, the tapered surface permits greater movement to the fasteners during the upward and downward movement of lift member 264.

Referring now to FIG. 17 additional features of the invention are illustrated including a pair of upstanding locator extensions 274b which engage and surround the retainer support portion when the retainer support portion 228 is closed for firing a fastener. These locator extensions provide stable positioning and positive location of the retainer support portion 228 relative to the fastener support portion 274. In addition, as shown in FIGS. 17, tissue stop 274c is pivotally positioned with spring 274d to bias the tissue stop toward the upward position as shown in FIG. 18. One end of spring 274d engages a dip on tissue stop 274c and the other free end is fixedly positioned relative to fastener support 274. Thus tissue stop 274c prevents the tissue of the patient from extending inwardly to the hinge area of the apparatus thus preventing unwanted jamming of the tissue and providing a limit for location of the tissue. As noted the upwardly extending locator extensions 274b provide precise relative positioning of the retainer support portion 228 and the fastener support portion 274, facilitating precise positioning of the distalmost fastener and the distalmost retainer. The advantages of such precise positioning is clear as it helps ensure alignment with the upstanding piercing members of the fasteners with the receiving apertures of the retainers for engaged entry.

Although the endoscopic surgical instrument of the subject invention has been described and shown with respect to a preferred embodiment, it would be apparent to one of ordinary skill in the art that changes and modifications may be made thereto without departing from the spirit or scope of the invention.

What is claimed is:

1. Apparatus for endoscopic application of two-part surgical fasteners, each two-part surgical fastener including a fastener portion and a retainer portion, which comprises:

a) a handle assembly;

b) an endoscopic portion extending distally from said handle assembly and defining a longitudinal axis;

c) first and second support means for respectively supporting a plurality of fastener portions and retainer portions in respective opposed positions along the longitudinal axis;

d) means for simultaneously advancing such fastener portions and retainer portions in a distal direction along said longitudinal axis while maintaining the opposed positions thereof;

e) fastener applying means for individually moving such fastener portions toward such retainer portions in a direction which is generally transverse to the direction of simultaneous advancement and into engagement with one another for application to body tissue; and f) means for sealing the apparatus to obstruct the passage of gaseous media.

2. Apparatus as recited in claim 1, wherein the means for sealing the apparatus is disposed in the endoscopic portion for inhibiting the egress of insufflation gas therethrough.

3. Apparatus as recited in claim 1, further comprising approximating means for moving the retainer portion support means and the fastener portion support means into close cooperative alignment.

4. Apparatus as recited in claim 3, wherein the support means for respectively supporting the plurality of fastener portions and retainer portions of the two-part surgical fasteners comprises first and second arms adapted for maintaining the retainer and the fastener portions.

5. Apparatus as recited in claim 4, wherein the first support means includes a first channel and the second support means includes a second channel.

6. Apparatus as recited in claim 5, wherein the means for individually moving one of such fastener and retainer portions into engagement with the other includes a linkage assembly operatively connected to the handle assembly.

7. Apparatus as recited in claim 6, wherein the linkage assembly includes a camming link and a pivoting link operatively associated with the camming link, wherein the camming link comprises at least one cam member having an elongated body portion and a head portion depending angularly from the body portion, the head portion having an elongated cam slot defined therein.

8. Apparatus as recited in claim 7, wherein the pivoting link includes at least one elongated rocker member having opposed proximal and distal ends, the rocker member being pivotably connected to the second arm intermediate the proximal and distal ends of the rocker member, the rocker member including lifting means for moving a fastener portion disposed at the distal end thereof and a cam follower connected to the proximal end thereof and adapted for translation relative to the cam slot defined in the cam member.

9. Apparatus as recited in claim 8, wherein the lifting means includes a lift member having a shelf defined therein for accommodating a fastener portion of one of the two-part surgical fasteners and the approximating means is operatively connected to the handle assembly and includes at least one elongated draw bar operatively connected to the first arm, the approximating means further including an elongated cam groove formed in a portion of the second arm and a camming pin connecting the draw bar to the first arm through the cam groove.

10. Apparatus as recited in claim 9, wherein the supporting means includes means for movably supporting the lifting means, the lifting means including a pair of rail members extending generally transversely of the longitudinal axis of the endoscopic portion, and at least two apertures for reception of the rail members to movably support the lifting means.

11. Apparatus for endoscopic application of two-part surgical fasteners each such fastener having a fastener portion and a retainer portion, which comprises:

a) an elongated endoscopic portion defining a longitudinal axis;

b) a plurality of fastener portions and a plurality of retainer portions supported in respective opposed positions along the longitudinal axis;

c) a fastener applying assembly including a mechanism for simultaneously advancing the fastener portions and retainer portions distally along the longitudinal axis defined by the endoscopic portion while maintaining the opposed positions thereof to position a distalmost fastener portion and a distalmost retainer portion for application to body tissue, and a mechanism for individually moving the fastener portions into engagement with the retainer portions in a direction transverse to their direction of simultaneous advancement; and d) a gaseous seal disposed within the endoscopic portion to inhibit the egress of gas therethrough.

12. Apparatus as recited in claim 11, further comprising an actuating member associated with a proximal end portion of the endoscopic portion for actuating the fastener applier.

13. Apparatus as recited in claim 12, wherein the plurality of fastener portions are aligned relative to the plurality of retainer portions such that a distalmost fastener portion is opposite a distalmost retainer portion.

14. Apparatus as recited in claim 13 further comprising a fastener supporting portion and a retainer supporting portion pivotably mounted with respect to each other to be approximated into close cooperative alignment.

15. Apparatus as recited in claim 14 wherein the fastener supporting portion and the retainer supporting portion are pivotable into close cooperative alignment from a location spaced proximal of the location of application of the fastener to body tissue.

16. Apparatus for endoscopic application of two-part surgical fasteners, each of such two-part surgical fasteners having a fastener portion and a retainer portion, which comprises:

a) a handle assembly;

b) an endoscopic portion extending distally from the handle assembly and defining a longitudinal axis;

c) fastener portion supporting means associated with a distal end portion of the endoscopic portion for supporting a plurality of the fastener portions of such two-part surgical fasteners;

d) retainer portion supporting means for supporting a plurality of such retainer portions of the two-part surgical fasteners in opposed positions relative to the fastener portions to facilitate the cooperative registration thereof;

e) approximating means operatively connected to the handle assembly for moving the retainer portion supporting means and the fastener portion supporting means into close cooperative alignment wherein an outer dimension of the retainer portion supporting means and the fastener portion supporting means is approximately equal to an outer dimension of the endoscopic portion; and f) driving means operatively connected to the handle assembly for simultaneously advancing the fastener portions and retainer portions distally within the respective fastener supporting means and retainer supporting means along the longitudinal axis while maintaining the opposed positions thereof and for individually moving at least one of such fastener portions and retainer portions into engagement with the other in a direction transverse to their direction of simultaneous advancement.

17. Apparatus as recited in claim 16, wherein the fastener portion supporting means supports a plurality of such fastener portions formed of a bioabsorbable material and the retainer portion supporting means supports a plurality of such retainer portions formed of a bioabsorbable material.

18. Apparatus as recited in claim 17, wherein the bioabsorbable material is selected from a group consisting of polymers of lactide, glycolide, p-dioxanone, polyester and polyamino acid.

19. Apparatus for endoscopic application of two-part surgical fasteners, each two-part surgical fastener including a fastener portion and a retainer portion, which comprises:

a) a handle assembly;

b) an endoscopic portion extending distally from the handle assembly and defining a longitudinal axis;

c) means for supporting a plurality of fastener portions and retainer portions in respective opposed positions along the longitudinal axis;

d) means for simultaneously advancing such fastener portions and retainer portions distally along the longitudinal axis while maintaining the opposed positions thereof prior to application of each of the surgical fasteners to body tissue;

e) fastener applying means for individually moving only the distalmost of the fastener portions toward the distalmost of the retainer portions in a direction transverse to the direction of simultaneous advancement and into engagement for application to body tissue in a single surgical fastener firing sequence; and f) means for sealing the apparatus to obstruct the passage of gaseous media.

20. Apparatus for endoscopic application of two-part surgical fasteners each having a fastener portion and a retainer portion, which comprises:

a) an elongated endoscopic portion defining a longitudinal axis;

b) a plurality of fastener portions and a plurality of retainer portions supported in respective opposed positions along the longitudinal axis;

c) a fastener applying assembly including a mechanism for simultaneously advancing the fastener portions and the retainer portions distally along the longitudinal axis while maintaining the opposed position thereof to position a distalmost fastener portion and a distalmost retainer portion for application to body tissue prior to application of the surgical fasteners to body tissue, and a mechanism for individually moving only the distalmost of the fastener portions into engagement with the distalmost of the retainer portions in a direction transverse to the direction of their simultaneous advancement in a single surgical fastener firing sequence; and d) a gaseous seal disposed within the endoscopic portion for inhibiting the egress of gas therethrough.

21. Apparatus as recited in claim 20, further comprising an actuating member associated with a proximal end portion of the endoscopic portion for actuating the fastener applier.

22. Apparatus as recited in claim 21, wherein the plurality of fastener portions are aligned relative to the plurality of retainer portions such that a distalmost fastener portion is opposite a distalmost retainer portion.

23. Apparatus as recited in claim 22 further comprising a fastener supporting portion and a retainer supporting portion pivotably mounted with respect to each other to be approximated into close cooperative alignment.

24. Apparatus as recited in claim 23 wherein the fastener supporting portion and the retainer supporting portion are pivotable into close cooperative alignment from a location spaced proximally from the location of application of the fastener to body tissue.

* * * * *